US009435895B2

(12) United States Patent
Ruschin et al.

(10) Patent No.: US 9,435,895 B2
(45) Date of Patent: Sep. 6, 2016

(54) MULTI-MODALITY DOSIMETER FOR USE WITH ARC-BASED RADIOTHERAPY QUALITY ASSURANCE PHANTOM

(71) Applicants: Mark Ruschin, Toronto (CA); Alexander Lightstone, Thornhill (CA); Ian Parkinson, Scarborough (CA); Harry Easton, Unionville (CA); David Beachey, Toronto (CA); Anthony Kim, North York (CA)

(72) Inventors: Mark Ruschin, Toronto (CA); Alexander Lightstone, Thornhill (CA); Ian Parkinson, Scarborough (CA); Harry Easton, Unionville (CA); David Beachey, Toronto (CA); Anthony Kim, North York (CA)

(*) Notice: Subject to any disclaimer, the term of this patent is extended or adjusted under 35 U.S.C. 154(b) by 0 days.

(21) Appl. No.: 14/702,148

(22) Filed: May 1, 2015

(65) Prior Publication Data

US 2015/0316657 A1 Nov. 5, 2015

Related U.S. Application Data

(60) Provisional application No. 61/987,917, filed on May 2, 2014.

(51) Int. Cl.
| | |
|---|---|
| *G01D 18/00* | (2006.01) |
| *G01T 1/04* | (2006.01) |
| *G01T 1/08* | (2006.01) |
| *G01T 1/161* | (2006.01) |
| *G01T 7/00* | (2006.01) |
| *A61N 5/10* | (2006.01) |

(52) U.S. Cl.
CPC ............... *G01T 1/04* (2013.01); *A61N 5/1075* (2013.01); *G01T 1/08* (2013.01); *G01T 1/161* (2013.01); *G01T 7/005* (2013.01); *A61N 5/1081* (2013.01); *A61N 2005/1076* (2013.01)

(58) Field of Classification Search
CPC . A61B 6/583; A61N 2005/1076; G01T 1/08
See application file for complete search history.

(56) References Cited

U.S. PATENT DOCUMENTS

| 2003/0231740 | A1* | 12/2003 | Paliwal et al. | 378/167 |
| 2007/0020793 | A1* | 1/2007 | Adamovics | 438/48 |
| 2010/0137709 | A1* | 6/2010 | Gardner et al. | 600/426 |

FOREIGN PATENT DOCUMENTS

GB 811492 * 4/1959

OTHER PUBLICATIONS

CIRS catalog, "Xsight Lung Tracking Phantom Kit & 4D Planning Phantom," 2013, 8 pages.*

* cited by examiner

*Primary Examiner* — Kiho Kim
(74) *Attorney, Agent, or Firm* — Quarles & Brady, LLP

(57) ABSTRACT

A dosimeter that is configured to assist with patient-specific quality assurance ("QA") in arc-based radiotherapy, such as stereotactic radiotherapy, is provided. The dosimeter facilitates acquiring multiple different dosimetric measurements simultaneously. For instance, the dosimeter can be configured to acquire dosimetric measurements from multiple different modalities, including gel dosimetry and film dosimetry, and is configured for simultaneous use with a diode-array QA phantom.

16 Claims, 3 Drawing Sheets

PLANNED DOSE              FILM IMAGE

MULTI-MODALITY DOSIMETER FOR USE WITH ARC-BASED RADIOTHERAPY QUALITY ASSURANCE PHANTOM

CROSS-REFERENCE TO RELATED APPLICATIONS

This application claims the benefit of U.S. Provisional Patent Application Ser. No. 61/987,917, filed on May 2, 2014, and entitled "MULTI-MODALITY DOSIMETER FOR USE WITH ARC-BASED RADIOTHERAPY QUALITY ASSURANCE PHANTOM."

BACKGROUND OF THE INVENTION

The field of the invention is systems and methods for measuring radiation for radiation therapy. More particularly, the invention relates to systems and methods for measuring and localizing radiation dose in a quality assurance ("QA") phantom useful for arc-based radiation therapy.

The current standard QA device for arc-based radiation treatment systems is a cylindrical diode array manufactured by Sun Nuclear (Sun Nuclear Inc., Melbourne, Fla., USA). The limitation of this device is that it measures and verifies radiation dose around a cylindrical surface, and not directly within the lesion being treated. Additionally, this diode array is not suitable for measuring dose in very small lesions, such as small brain metastases. Radiochromic film has been demonstrated to be very useful verifying radiation dose in small targets, but there is no standard test object that incorporates film into the measurement.

There is a need for an accurate measurement of dose in a stationary object that simulates a patient, the stationary object herein referred to and well known as a phantom, while a radiation therapy delivery system moves with respect to the phantom, and that such a measurement results in a three dimensional (3-D) dose map that is coherent at any beam angle relative to the phantom.

Quality assurance (QA) methods have incorporated film, a passive array, and electronic active detector arrays, which provide two dimensional (2-D) planes orthogonal to the beam axis and result in a 2-D dose map of the field. With the evolution of delivery techniques where the source rotates (or moves) while the patient remains stationary (such as Rapid Arc™, HI-ART™, VMA™, Single Arc Therapy™ (SAT), CyberKnife™, and Renaissance™), the 2-D array no longer provides the same coherent dosimetric information as it did when the beam projection was restricted to be normal to the array plane. At one beam angle, the 2-D array appears as a plane, but with a 90 degree rotation of the radiation source, the 2-D array appears as a linear array with many lines of detectors at different depths in the array. This creates a dose information weighting problem with the detector sampling dose at depths and densities that change significantly at and near the vicinity of the beam axis as the beam rotates around the array.

There is also a need, in this 3-D dosimetry system, to measure and store the dose during specific time segments throughout the duration of the radiation delivery to the phantom, and to have no significant measurement limit on the total dose delivery. With movement of the source comes a temporal feature to the dose delivery because the position of the source is time dependent and the position of the source is a factor in the dose distribution. Any rigorous QA solution that verifies the dose delivery should do so with a number of finite "time segment" dose measurement distributions that can be compared to the desired dose distribution during any particular segment in time, or over a beam angle which is a function of time in the delivery system. Furthermore, with time segmented dose data in three dimensions and beam edge proximities to detectors, which is provided by embodiments of the present invention, it is possible to determine the source angle by ray tracing through 3-D dose distributions, and verify the source angle with the intended angle during that time segment. Without time segment data, the measured dose distribution becomes a composite of the entire dose delivery from all angles, which in itself, can be compared to the intended dose distribution, but with limited QA benefit. The composite blurs the delivery error that occurred at any given angle, just as it does in conventional IMRT QA when all fields are summed together into a composite. A current American Association of Physicists in Medicine (AAPM) task group activity (TG119) has discussed recommending against composite QA and recommending field measurement QA, but is not published at the time of this writing. Therefore, comparison of time segment measurements of dose delivery with planned dose delivery during the time segment is analogous to field QA in conventional IMRT.

There is also a need, in this 3-D dosimetry system, for a dose measurement that can localize a portion of the beam edges that occur in modulated beams and open fields. The beam edge defines the dose location and any QA solution that verifies the dose delivery preferably verifies both the magnitude of the dose and its location. This becomes particularly desirable when the source of the beam itself is moving. Each time segment preferably contains a quantifiable location of the beam during that time segment. The beam edge measurement will generally depend upon the spatial resolution of the radiation detector; therefore the "spatial frequency" of a detector is preferably high enough to sample a location in the beam edge without averaging the edge over a significant distance that would defeat the purpose of the QA localization.

There is also a need to coordinate this dose location to a spatial location defined by an imaging system, with image-guided radiotherapy (IGRT) being one such application. The patient imaging system locates anatomical landmarks (repeatably using independent markers, by way of example) that may be used to set up a patient and to monitor motion in a treatment simulator system or for image guidance during radiation therapy (IGRT). In this 3-D dosimetry system, there is a need to determine, by means of a patient imaging system, the positions of the detectors in the array. The positions can be determined by an imageable object (the detector object itself or an object whose position is known relative to the detector) that can be imaged by the patient imaging system, with spatial resolution that satisfies the localization requirements of the beam in the patient anatomy. The image location of the detector and the beam location measurement with the detector becomes a QA verification of the imaging and delivery coordinates. Such a basic concept was demonstrated and published by D. Letourneau3, Med Phys 34(5) May 2007 "Integral Test Phantom for Dosimetric Quality Assurance of Image Guided and Intensity Modulated Stereotactic Radiotherapy." The work that Letourneau published resulted from a prototype device designed and built by Sun Nuclear Corporation with detectors in a radial plane (i.e. in the interior of the phantom). Unlike the radial plane prototype, the array geometry described for embodiments of the present invention does not require interior detectors (i.e. detectors at various radial locations). However, that does not prevent similar utilization of detectors on a 3-D surface for localization of imaging coordinates and beam location coordinates.

Film that is configured in a phantom for 3-D measurements will satisfy some needs, but not the time segment or detector imaging needs. This was nearly demonstrated in a paper by Paliwal[4] with a phantom that provided a 3-D location for film in a spiral wrap that started near the circumference and then spiraled in toward the interior of the phantom. This was commercialized by Gammex[5]. The depth of the film continuously changed depending upon the beam angle entrance; therefore the data did not result in a coherent dose measurement as later addressed in this document. As will be later described for one embodiment of the present invention satisfying this need, if film is wrapped into a cylindrical geometry that is concentric with a cylindrical phantom, then this would result in a coherent dose measurement because the beam would see the same measurement geometry, regardless of the beam angle, assuming the beam is normal to the cylinder axis.

Yet further, the 2-D arrays measure dose distributions in time segments can locate beam edges in those time segments, but cannot measure a coherent dose distribution when the source location moves with respect to array perpendicularity from one time segment to another, as will be further addressed later in this document. Such arrays could, in theory, satisfy the need to localize the imaging system to beam edges if the required design parameters satisfy the need. However, the need is rarely satisfied if by chance the features needed are in the design but the intention was not considered in the design. For example, the geometric projection of an ion chamber (on an array) that does not remain coherent with the source movement will have a spatial resolution that may change and render the localization of beam edge as not sufficient resolution to be useful. Therefore, while there may be some unintended capability to locate a beam edge in varying time segments does not mean that it has sufficient capability to satisfy the intended use. Another example is an array of detectors, as in the Delta4[6] design, that have sufficient geometric properties to satisfy beam edge localization but the measurement geometry of the array itself does not remain coherent as the source moves from one time segment to another.

SUMMARY OF THE INVENTION

The present invention overcomes the aforementioned drawbacks by providing a dosimeter that includes a film assembly and a film holder. The film assembly includes a plurality of film inserts arranged in a parallel stacked arrangement, each film insert being configured to receive a film. The film holder is configured to receive the film assembly and has a cylindrical outer surface that is sized to be received by a bore of a cylindrical quality assurance phantom. The film assembly can also be configured to include other dosimetric tools, including one or more gel dosimeters.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Described here is a dosimeter that is configured to assist with patient-specific quality assurance ("QA") in arc-based radiotherapy, such as stereotactic radiotherapy. The dosimeter described here facilitates acquiring multiple different dosimetric measurements simultaneously. For instance, the dosimeter can be configured to acquire dosimetric measurements from multiple different modalities, including gel dosimetry and film dosimetry, and is configured for simultaneous use with a diode-array dosimeter.

In particular, the dosimeter is capable of simultaneously acquiring multiple film measurements with a diode-array measurement. This is accomplished by fabricating a film holder that fits precisely within the central bore of the cylindrical diode array. In some other embodiments, other dosimetric measurements can also be simultaneously acquired with the film and diode-array measurements. As one example, gel dosimetry measurements can also be obtained. As another example, ion chamber measurements can also be obtained.

The dosimeter is designed specifically for measuring radiation dose distributions on film as an added patient-specific QA to a diode-array test for arc-based stereotactic radiotherapy. The dosimeter can also be used, however, to commission new radiation delivery techniques and can be adapted to include heterogeneous media, such as lung tissue for lung stereotactic radiotherapy.

Figure 1:
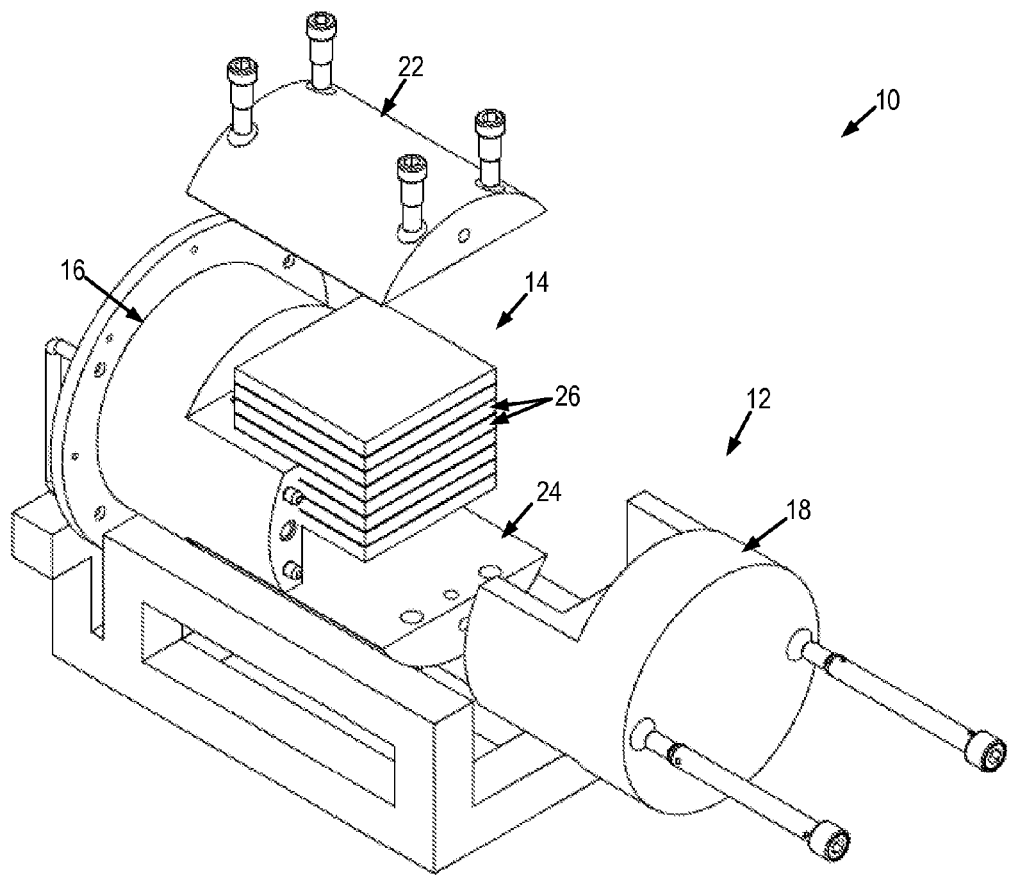
FIG. 1 is an illustration of an example dosimeter configured to be inserted into a central bore of a cylindrical, diode-array quality assurance phantom.
Figure 2:
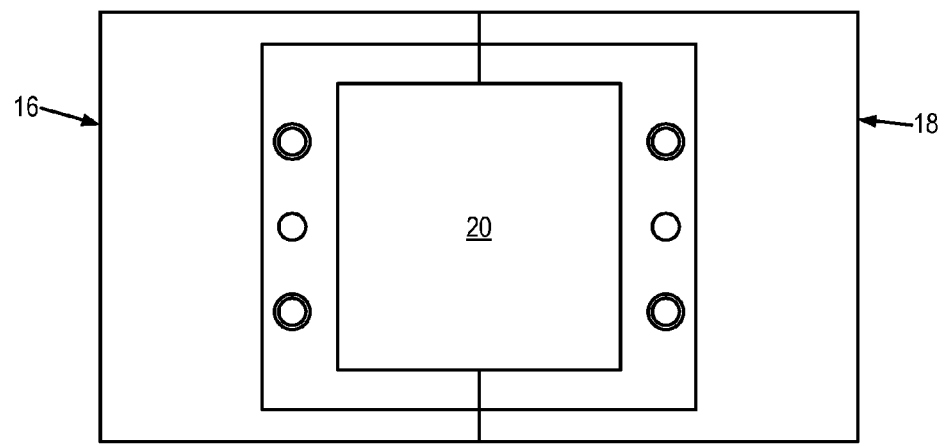
FIG. 2 is a plan view of a film holder that forms a part of the dosimeter of FIG. 1.

Referring to FIGS. 1 and 2, a dosimeter 10 generally includes a film holder 12 that is configured to receive a film assembly 14. The film holder 12 is shaped to have a generally cylindrical outer surface, such that the film holder 12 can be securely placed in the bore of a cylindrical QA phantom that includes an array of diode-based radiation detectors. An example of such a cylindrical QA phantom is the ArcCHECK® cylindrical detector array (Sun Nuclear; Melbourne, Fla., US). The cylindrical QA phantom is well-suited for rotational dosimetry applications, such as performing QA for arc-based radiation therapy systems, which may include intensity modulated arc therapy ("IMAT") systems, volumetric modulated arc therapy ("VMAT") systems, flattening filter free ("FFF") beam delivery systems, tomotherapy systems, or even traditional intensity modulated radiation therapy ("IMRT") systems.

The film holder 12 is preferably constructed to allow easy disassembly, such that the film assembly 14 can be readily positioned in and removed from the film holder 12. In some embodiments, the film holder 12 is composed of acrylic; however, other suitable materials could also be used for construction of the film holder 12.

In some embodiments, the film holder 12 is composed of an end cap 16 and a front cap 18 that opposes the end cap 16. The end cap 16 and front cap 18 are configured to be coupled together and to define a recessed region 20 that is sized and shaped to receive the film assembly 14. The film holder 12 may also include a top cap 22 and a bottom cap 24 that further define the generally cylindrical outer surface of the film holder 12. The top cap 22 and bottom cap 24 can be configured to be coupled to the end cap 16 and the front cap 18, as illustrated in FIG. 1.

The film assembly 14 is composed of a plurality of film inserts 26, or layers, that are generally arranged in a parallel stacked arrangement. In this configuration, the film assembly 14 provides multi-planar information about dose distribution in the interior of the cylindrical QA phantom into which the dosimeter 10 is configured to be inserted.

In some embodiments, the dosimeter 10 can be configured to receive other dosimetric tools, including dosimetry gel inserts. For example, the recessed region 20 in the film holder 12 can be sized to receive a dosimetry gel insert in addition to the film assembly 14. In other embodiments, it may be possible to incorporate a gel dosimeter into the film assembly 14, such as by replacing one or more of the film inserts 26 with a gel dosimeter, or by otherwise incorporating a gel dosimeter into a given film insert 26.

Figure 3:
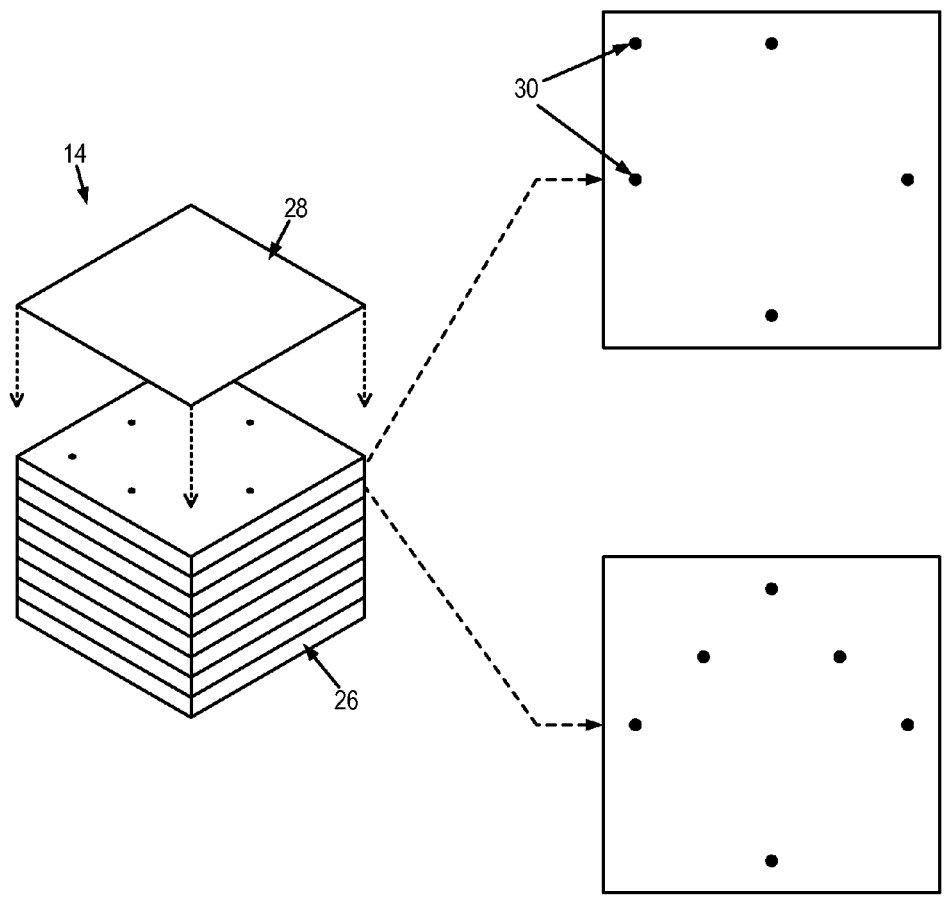
FIG. 3 is an illustration of an example film assembly that forms a part of the dosimeter of FIG. 1.

Referring now to FIG. 3, each film insert 26 in the film assembly 14 is configured to receive a film 28, which may be radiochromic film. In some embodiments, each film insert 26 includes markers 30, such as pins, that will imprint the film 28 when the film 28 is placed on the film insert 26. These markers 30 are arranged differently for each film insert 26, as illustrated in FIG. 3, such that the imprint on the film 28 for a given film insert 26 will be unique relative to the other film inserts 26. In this manner, the imprints made on the film 28 can be used for orientation and alignment when analyzing the individual films 28.

Having described the general structure of the dosimeter, an example of how the dosimeter can be used is now provided. For a given patient radiation therapy plan, the dose distribution is computed on a CT scan of the diode array containing the dosimeter. The dose distribution calculated in the patient plan is somewhat altered when re-computed on the diode-array phantom. The radiation is then delivered to the diode array containing the dosimeter with blank pieces of film pre-loaded in the film assembly at the appropriate planes of interest. After radiation delivery, both the diode-array measurements and the film measurements are compared to the planned dose distribution. In some configurations, the film measurement results in a coronal view representation of the dose distribution, which when compared to the planned distribution can be analyzed using dose agreement and distance-to-agreement ("DTA") dose metrics.

Figure 4:
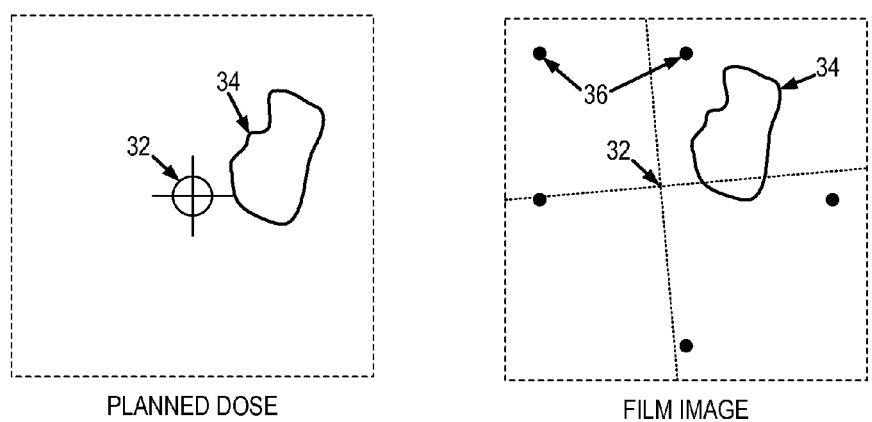
FIG. 4 is an illustration comparing a planned dose distribution and a film measurement obtained with a film dosimeter.

Referring to FIG. 4, an example comparison between a clinical treatment plan and a film measurement is illustrated. The plane-of-interest ("POI") or region-of-interest ("ROI") in the planned dose distribution can be loaded and displayed to indicate the isocenter 32, which facilitates registration of the film or other dosimetric images with the planned dose distribution 34. The markers 30 are depicted in the film image (shown as marks 36) and can provide an indication of the iso center of the film image, which in turn can be used to determine the deviation of the film image relative to the isocenter 32 of the clinical treatment plan. Using this information, the film image and clinical treatment plan can be co-registered.

Figure 5:
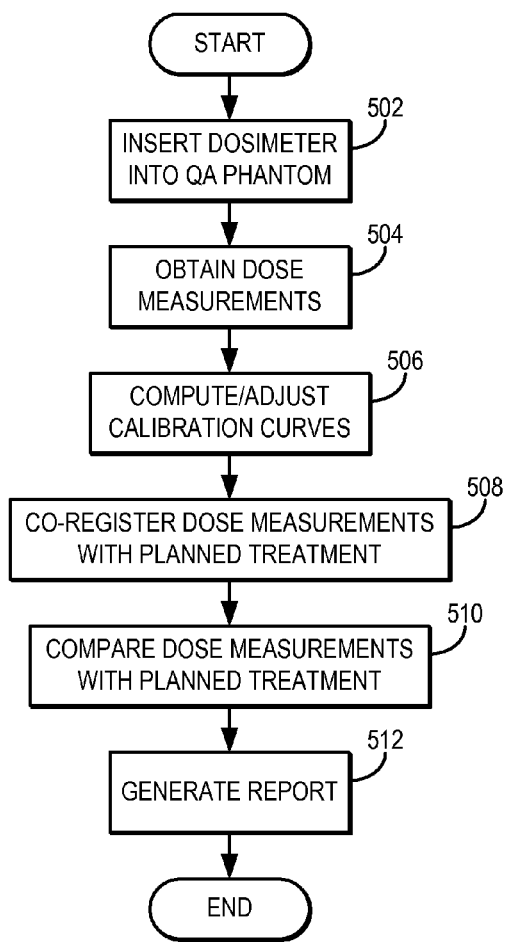
FIG. 5 is a flowchart setting forth the steps of an example method for analyzing dose measurement data obtained with a dosimeter and cylindrical, diode-array quality assurance phantom.

Referring now to FIG. 5, a flowchart setting forth the steps of an example method for using the dosimeter of the present invention is illustrated. The dosimeter is inserted into the bore of a cylindrical diode array QA phantom, as indicated at step 502. A dose measurement is then obtained, as indicated at step 504. In some instances, a user may want to scan a given measurement multiple times to minimize scanner electronic noise, thereby acquiring multiple different dose measurements. In these instances, the average of the multiple different dose measurements can be averaged to reduce the electronic noise, and the average can be stored as the dose measurement.

The dose measurement includes a measurement obtained with the diode array and multiple measurements obtained with the dosimeter. For example, as described above, the dosimeter can obtain film measurements in multiple different planes-of-interest and can obtain measurements from other dosimetric tools that may be included in the dosimeter, such as gel dosimetry measurements or ion chamber measurements. The multiple different dose measurements can then be integrated for analysis.

In some embodiments, the dose measurements can be analyzed using a software package that can handle high throughput and complex scenarios encountered in radiotherapy, in a streamlined fashion. It is contemplated that the software will enable performing detailed analyses that can be tailored to different clinical techniques. The software also has the possibility to visualize the different dosimetry modalities in a single interface, and to combine effects of each different modality.

As part of the analysis of the multi-modality dose measurements, a scaled calibration curve may be generated, as indicated at step 506. In some embodiments, this step may include generating adjusted calibration curves based on current calibration films. This feature allows the user to scale the primary calibration curve based on a set of calibration films acquired during the measurement session. If no calibration films are acquired, the native calibration curve can be applied. The mean pixel value at each dose level is compared to the primary calibration curve, and a correction factor is applied to the primary calibration curve.

As a part of the analysis process, the dose measurement data can be co-registered with a clinical treatment plan, as indicated at step 508 and described above with respect to FIG. 4. The dose measurement data can then be compared with the clinical treatment plan, as indicated at step 510. As an example, absolute dose gamma and distance-to-agreement ("DTA") comparisons can be performed. Preferably, the gamma and DTA analysis done in absolute dose and not relative to maximum dose; however, comparisons relative to maximum dose can also be performed. In some embodiments, the analysis can determine uncertainties associated with the calibration curve and propagate those through measurements.

A report can then be generated based on the comparison of the dose measurement data with the clinical treatment plan, as indicated at step 512. As one non-limiting example, the generated report can include a computer-generated display of images of numerical information produced by or in connection with the comparison.

Figure 6:
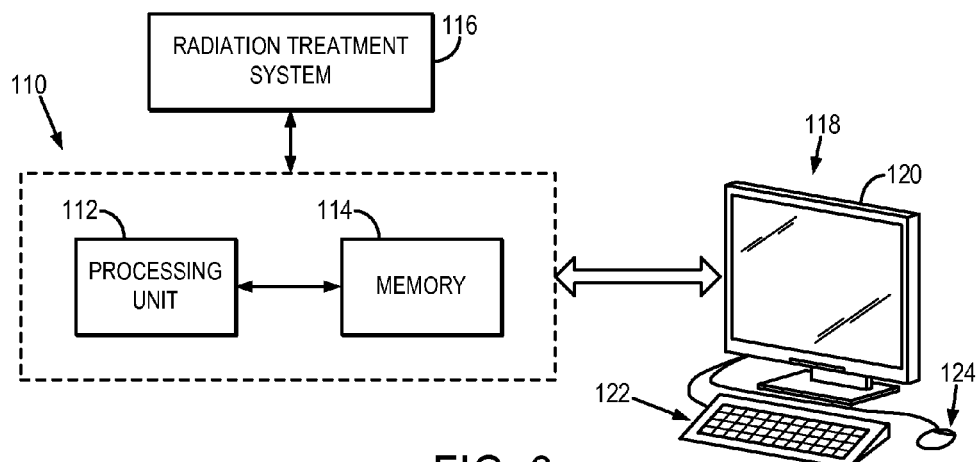
FIG. 6 is a block diagram of an example radiation treatment planning system, which may implement the method depicted in FIG. 5.

The methods described above can be suitably implemented using a radiation treatment planning system. Referring now to FIG. 6, an example of such a radiation treatment planning system 110 is illustrated. The radiation treatment planning system 110 is preferably in communication with one or more radiation treatment systems 112, which may include any suitable arc-based radiation treatment system.

The radiation treatment planning system 110 generally includes a memory 114 that is operably coupled to a processor unit 116. As an example, the processor unit 116 can be a commercially available computer processor, such as those described above. The processor unit is configured to carry out one or more of the steps of the methods described above.

As an example, the memory 114 can include a plurality of memory elements, or can include a single memory element. In general, the memory 114 is configured to store information regarding patient data, a clinical treatment plan, calibration curves, dose measurements obtained from the dosimeter and cylindrical diode-array QA phantom, and so on.

Preferably, the radiation treatment planning system 110 includes, or is otherwise in communication with, a user interface 118. As an example, the user interface 118 provides information to a user, such as a medical physicist. For example, the user interface 118 can include a display 120 and one or more input devices, such as a keyboard 122 and mouse 124.

The present invention has been described in terms of one or more preferred embodiments, and it should be appreciated that many equivalents, alternatives, variations, and modifications, aside from those expressly stated, are possible and within the scope of the invention.

The invention claimed is:

1. A dosimeter, comprising:
   a film assembly comprising a plurality of film inserts arranged in a parallel stacked arrangement, each film insert being configured to receive a film;
   a film holder configured to receive the film assembly and having a cylindrical outer surface that is sized to be received by a bore of a cylindrical QA phantom; and
   wherein each of the plurality of film inserts includes a plurality of markers configured to imprint a pattern on a film inserted in each film insert.

2. The dosimeter as recited in claim 1, further comprising a gel dosimeter insert, and wherein the film holder is further configured to receive the gel dosimeter insert.

3. The dosimeter as recited in claim 2, wherein the film assembly comprises the gel dosimeter insert in addition to the plurality of film inserts, wherein the gel dosimeter insert is also arranged in the parallel stacked arrangement.

4. The dosimeter as recited in claim 1, wherein the plurality of markers for each of the plurality of film inserts is arranged differently such that a different pattern is imprinted on a film inserted in each different film insert.

5. A non-transitory computer-implemented method for comparing dose measurements obtained with a multimodality dosimeter with a clinical treatment plan, the steps of the method comprising:
   (a) receiving dose measurement data in a computer system, the dose measurement data being obtained with a multimodality dosimeter;
   (b) generating a scaled calibration curve based on calibration data using the computer system;
   (c) generating scaled dose measurement data by scaling the received dose measurement data using the scaled calibration curve using the computer system;
   (d) co-registering the scaled dose measurement data, using the computer system, with a clinical treatment plan stored in a memory;
   (e) comparing the scaled dose measurement data with the clinical treatment plan using the computer system; and
   (f) generating a report based on comparing the scaled dose measurement data with the clinical treatment plan.

6. The non-transitory computer-implemented method as recited in claim 5, wherein the dose measurement data received in step (a) comprises multiple different dose measurements.

7. The non-transitory computer-implemented method as recited in claim 6, wherein step (a) comprises producing average dose measurement data by computing an average of the multiple different dose measurements and storing the average dose measurement data as the dose measurement data.

8. The non-transitory computer-implemented method as recited in claim 6 wherein the multiple different dose measurements comprise dose measurements obtained with multiple different dose measurement modalities.

9. The non-transitory computer-implemented method as recited in claim 8, wherein the multiple different dose measurement modalities include film measurements and gel dosimetry measurements.

10. The non-transitory computer-implemented method as recited in claim 9, wherein the film measurements include film measurements obtained in multiple different planes-of-interest.

11. The non-transitory computer-implemented method as recited in claim 5, wherein the calibration data used in step (b) comprises a plurality of calibration films.

12. The non-transitory computer-implemented method as recited in claim 5, wherein the calibration data used in step (b) comprises a native calibration curve.

13. The non-transitory computer-implemented method as recited in claim 5, wherein step (b) includes scaling a primary calibration curve based on the calibration data.

14. The non-transitory computer-implemented method as recited in claim 13, wherein the primary calibration curve is scaled by comparing a mean pixel value at each dose level in the received dose measurement data to the primary calibration curve and applying a correction factor to the primary calibration curve based on comparing the mean pixel value at each dose level to the primary calibration curve.

15. The non-transitory computer-implemented method as recited in claim 5, wherein step (e) includes comparing the scaled dose measurement data with the clinical treatment plan based on an absolute dose gamma comparison.

16. The non-transitory computer-implemented method as recited in claim 5, wherein step (e) includes comparing the scaled dose measurement data with the clinical treatment plan based on a distance-to-agreement comparison.

* * * * *